United States Patent [19]

Carpi et al.

[11] 4,002,753
[45] * Jan. 11, 1977

[54] 6-SUBSTITUTED 3-CARBETHOXYHYDRAZINOPYRIDAZINES

[75] Inventors: Carlo Carpi, S.Polo d'EnZa (Reggio Emilia); Luciano Dorigotti; Giorgio Pifferi, both of Milan, all of Italy

[73] Assignee: I.S.F. S.p.A., Milan, Italy

[ * ] Notice: The portion of the term of this patent subsequent to Dec. 9, 1992, has been disclaimed.

[22] Filed: Sept. 16, 1975

[21] Appl. No.: 613,865

Related U.S. Application Data

[63] Continuation-in-part of Ser. No. 447,523, March 4, 1974, Pat. No. 3,925,381.

[30] Foreign Application Priority Data

Mar. 7, 1973   Italy ................................. 21297/73

[52] U.S. Cl. ............................ 424/250; 260/250 A
[51] Int. Cl.² ................ C07D 237/20; A61K 31/50
[58] Field of Search ................ 260/250 A; 424/250

[56] References Cited

UNITED STATES PATENTS 3,925,381   12/1975   Carpi et al. .................... 260/250 A

*Primary Examiner*—Alton D. Rollins
*Assistant Examiner*—Mark L. Berch
*Attorney, Agent, or Firm*—Stevens, Davis, Miller & Mosher

[57] ABSTRACT

6-substituted 3-carbethoxyhydrazinopyridazines of the general formula:

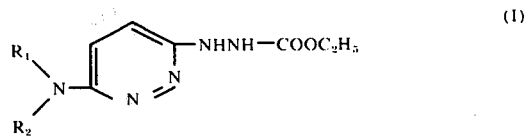

wherein $R_1$ and $R_2$, which may be the same or different, represent a lower alkyl group containing from 1 to 6 carbon atoms, an allyl group, a 2-hydroxyethyl group or a 2-hydroxypropyl group, as well as the pharmaceutically acceptable salts thereof. Also a method of preparation. These compounds have anti-hypertensive activity.

2 Claims, No Drawings

6-SUBSTITUTED 3-CARBETHOXYHYDRAZINOPYRIDAZINES

This application is a continuation-in-part of application Ser. No. 447,523 filed Mar. 4, 1974, now U.S. Pat. No. 3,925,381.

The present invention relates to new derivatives of pyridazine possessing remarkable pharmacodynamic properites. More particularly, the invention relates to new 6-substituted 3-carbethoxyhydrazinopyridazines of the general formula:

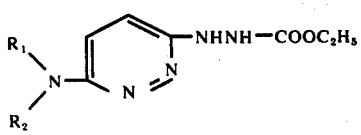
(I)

wherein $R_1$ and $R_2$, which may be the same or different, represent a lower alkyl group containing from 1 to 6 carbon atoms, an allyl group, a 2-hydroxyethyl group or a 2-hydroxypropyl group, as well as the pharmaceutically acceptable salts thereof with inorganic acids such as hydrochloric, hydrobromic, sulphuric acid etc., or with organic acids, such as acetic, succinic, benzoic, p-toluensulphonic acid etc.

It is known that some derivatives of 6-substituted 3-hydrazinopyridazine possess remarkable anti-hypertensive activity. However, the therapeutic applications of said drugs are limited by the fact that they cause tachycardia, headache, vertigo, etc., owing to the rapidity with which the hypotensive effect develops. Furthermore, repeated daily administrations are necessary to maintain the desired effect.

It has now been discovered that in the class of derivatives of formula (I) where a 2-carbethoxyhydrazinic group is contained in the molecule, the anti-hypertensive effect develops with a slow progression and is definitely more prolonged compared to similar drugs such as Hydralazine and Binazin.

Some illustrative results obtained in the renal hypertensive awaken rat according to the method of A. Grollman (Proc. Soc. Exptl. Biol. Med., 57, 102, 1944) are given in Table 1. The products were administered orally to groups of 4 rats for each dosage level. The arterial pressure was measured by bloodless method immediately before and at the 1st, 3rd, 5th, 7th, 12th, 24th, 36th, 48th and 60th hour after administration.

The evaluation of the acute toxicity was carried out in the mouse administering the products by the intraperitoneal route at 6 different dosage levels. The approximate $LD_{50}$ was determined thereafter.

The results listed in the above Table show that the compounds of the present invention display low toxicity, high activity, and possess the characteristic of a more gradual development of the hypotensive effect, as proved by the value of maximum effect appearance times. The higher values of the half effect time show furthermore the really exceptional duration of the hypotensive effect developed in the experimentally hypertensive animal.

The compounds of the invention and pharmaceutically acceptable salts thereof are useful as pharmaceuticals and are characterized by activity as hypertensive agents.

These compounds can be used in the form of conventional pharmaceutical preparations; for example, the aforesaid compounds can be mixed with conventional organic or inorganic, inert pharmaceutical carriers suitable for parenteral or enteral administration such as, for example, water, gelatin, lactose, starch, magnesium stearate, talc, vegetable oil, gums, polyalkylene glycols, vaseline or the like. They can be administered in conventional pharmaceutical forms, e.g. solid forms, for example tablets, dragees, capsules and the like; or in liquid forms, for example, injectable solutions, suspensions or emulsions. Moreover, the pharmaceutical compositions containing compounds of this invention can be subjected to conventional pharmaceutical expedients such as sterilisation and can contain conventional pharmaceutical excipients such as preservatives, stabilizing agents, wetting agents, emulsifying agents, salts for the adjustment of osmotic pressure or buffers. The compositions can also contain other therapeutically active materials.

A suitable pharmaceutical dosage unit can contain from about 1 to 5 mg daily of the aforesaid compounds and due to their long-lasting effect this dosage can be also administered in a single daily dose.

The present invention furthermore relates to a process for the preparation of the new pyridazine derivatives of formula (I), comprising the reaction between a compound of the formula:

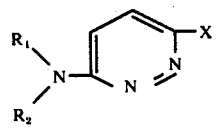
(II)

wherein $R_1$ and $R_2$ have the above meaning and X represents a chlorine or bromine atom and monocarbethoxyhydrazine:

$$H_2N-NH-COOC_2H_5 \qquad (III)$$

Derivatives of formula (II) used as starting materials are known, as is monocarbethoxyhydrazine (III). The compounds of formula (II) are warmed up with two equivalents of monocarbethoxyhydrazine preferably in

TABLE

| Compound | Mouse $LD_{50}$ mg/Kg i.p. | $ED_{20}$ x mg/kg orally | Renal hypertensive awaken rat | |
|---|---|---|---|---|
| | | | Time in hours of maximum effect appearance | Time in hours of half effect appearance |
| Example 3 | 700 | 1 | 5 | 36 |
| Example 5 | 300 | 1 | 5 | 48 |
| Example 6 | 700 | 1 | 5 | 36 |
| Binazin | 500 | 7 | 3 | 20 |
| Hydralazine | 100 | 3 | 1 | 5 | x $ED_{20}$ = dose producing a 20% fall in pressure compared to the basal value.

the absence of solvents and at a temperature ranging between 140°–160° C. The excess monocarbethoxyhydrazine serves to help the reaction, blocking the hydrochloric acid which forms during the condensation with the compounds of formula (II). The duration of the reaction is not critical but the operation is preferably carried out during a short period of time ranging from about a half an hour to about one hour of heating. When heating is over, the reaction mass is taken up with a protic solvent, preferably aqueous or alcoholic, and the base of formula (I) is made free of alkalinization with suitable basic agents such as bicarbonates, carbonates, or alcoholates of alkali metals. The isolation of the final product is carried out by precipitation, concentration or extraction according to the usual methods, and successive purification can be carried out by conventional crystallization or chromatography.

The following Examples, which are not limitative, serve to illustrate the present invention.

EXAMPLE 1

3-(2-Carbethoxyhydrazino)-6-dimethylaminopyridazine hydrochloride

A mixture of 1.57 g (0.01 moles) 3-chloro-6-dimethylaminopyridazine and 2.08 g (0.02 moles) monocarbethoxyhydrazine is warmed up for half an hour at 160° C. The resulting mixture is cooled, water added thereto, the solid which separates filtered away and the filtrate neutralized with $NaHCO_3$ until a final pH 7. The mixture is then extracted with cloroform, the organic extract dried over sodium sulphate and the solvent evaporated. The residual oil is purified by chromatography on silica gel, eluting with a mixture of chloroform:methanol 8.5:1.5. The unitary fractions on thin layer chromatography with the same Rf are collected together, evaporated and the residue treated while warm with ethyl ether, and the residue filtered off. By addition of hydrogen chloride to the filtrate, 3-(2-carbethoxyhydrazino)-6-dimethylaminopyridazine hydrochloride precipitates with good yields melting at 215°–217° C (with dec).

I.R. Spectrum (mineral oil, $cm^{-1}$): 3200 (NH), 1715 (C=O carbamate), 1595 (pyridazinic ring), 840 (two ortho-aromatic hydrogens).

Analysis: Calculated for $C_9H_{15}N_5O_2.HCl$: C, 41.30; H, 6.16; N, 26.76; Cl, 13.55. Found: C, 41.59; H, 6.20; N, 26.77; Cl, 13,29.

EXAMPLE 2

3-(2-Carbethoxyhydrazino)-6-[N-(2-hydroxyethyl)-methylamino]-pyridazine

A mixture of 1.87 g (0.01 moles) 3-chloro-6-[N-(2-hydroxyethyl)-methylamino]-pyridazine and 2.08 g (0.02 moles) monocarbethoxyhydrazine is warmed up to 155° C and kept at this temperature for half an hour. The product is cooled and dissolved in water, alkalinized by addition of solid potassium carbonate and the aqueous solution saturated by adding sodium chloride. A flocky precipitate separates which is subsequently collected by filtration and crstallized from ethanol, to give with good yields 3-(2-carbethoxyhydrazino)-6-[N-(2-hydroxyethyl)methylamino]-pyridazine melting at 131°–133° C. I.R. Spectrum (mineral oil, $cm^{-1}$); 3320–3080 (OH and NH), 1715 (C=O carbamate), 1500 (pyridazinic ring), 840 (two ortho aromatic hydrogens).

Analysis: Calculated for $C_{10}H_{17}N_5O_3$: C, 47.05; H, 6.71; N, 27.43. Found: C, 46,89; H, 6.81; N, 27.74.

EXAMPLE 3

3-(2-Carbethoxyhydrazino)-6-[N-(2-hydroxypropyl)-methylamino]-pyridazine

A mixture of 6 g (0.029 moles) 3-chloro-6-[n-(2-hydroxypropyl)-methylamino]-pyridazine and 6.2 g (0.069 moles) monocarbethoxyhydrazine is warmed up to 145° C and kept at this temperature for 1 hour. After cooling, the residue is taken up in water and the solution extracted with chloroform. The aqueous phase is cooled and treated with potassium carbonate until complete precipitation. The precipitation is collected and purified by crystallization from ethanol to give with good yields 3-(2-carbethoxyhydrazino)-6-[N-(2-hydroxypropyl)-methylamino]-pyridazine melting at 150°–152° C.

Analysis: Calculated for $C_{11}H_{19}N_5O_3$: C, 49.06; H, 7.11; N, 26.00. Found: C, 49.15; H, 7.50; N, 26.04.

EXAMPLE 4

3-(2-Carbethoxyhydrazino)-6-[di-(2-hydroxyethyl)-amino]-pyridazine hydrochloride A mixture of 4.34 g (0.02 moles) 3-chloro-6-bis-(2-hydroxyethyl)-aminopyridazine and 4.16 g (0.04 moles) monocarbethoxyhydrazine is warmed up to 140° C and kept at such temperature for one hour. The mixture is cooled, methanol added thereto until solution, and neutralized with a methanol solution of sodium methoxide to pH 7. The solvent is evaporated and the residual oil purified by chromatography on silica gel column, eluting with a mixture of chloroform-methanol 8.5:1.5. The unitary fractions on thin layer chromatography with the same Rf are collected together, evaporated and the residue, taken up with acetone, is acidified with hydrogen chloride. Good yields of 3-(2-carbethoxyhydrazino)-6-[di-(2-hydroxyethyl)-amino]-pyridazine hydrochloride melting at 162°–165° C (with dec.) are obtained.

I.R. Spectrum (mineral oil, $cm^{-1}$): 3450–3200 (OH and NH), 1710 (C=O carbamate) 1595 (pyridazinic ring), 840 (two ortho aromatic hydrogens).

Calculated for $C_{11}H_{19}N_5O_4.HCl$: C, 41.06; H, 6.26; Cl, 11.01; N, 21.76. Found: C, 40.90; H, 5.90; Cl, 10.50; N, 22.41.

EXAMPLE 5

3-(2-Carbethoxyhydrazino)-6-diallylaminopyridazine

A mixture of 4.18 g (0.02 moles) 3-chloro-6-diallylaminopyridazine and 4.16 g (0.04 moles) monocarbethoxyhydrazine is warmed up to 140° C and kept at this temperature for 1 hour. The mixture is taken up with cool water and sodium carbonate is added until neutral pH. It is then extracted with methylene chloride, the organic extracts collected together, dried over sodium sulphate and concentrated. The residual oilis purified by chromatography on silica gel column, eluting with a mixture of chloroform-methanol 9.5:0.5. The unitary fractions on thin layer chromatography with the same Rf are collected together; the solvent is eliminated by evaporation and a yellow oil formed by a 3-(2-carbethoxyhydrazino)-6-diallylaminopyridazine is obtained.

I.R. Spectrum (mineral oil, cm$^{-1}$); 3350–3100 (NH), 1715 (C=O carbamate), 1645 (—CH=CH$_2$), 830–825 (two ortho aromatic hydrogens).

Analysis: Calculated for $C_{13}H_{19}N_5O_2$: C, 56.30; H, 6.90; N, 25.25. Found: C, 56.01; H, 6.80; N, 25.48.

Example 6

3-(2-Carbethoxyhydrazino)-6-[N-(2-hydroxypropyl)ethylamino]-pyridazine

A mixture of 11 g 3-chloro-6-[N-(2-hydroxypropyl)ethylamino]pyridazine which can be be prepared as described in Example 4 of U.S. Pat. No. 3,769,278 and 11 g monocarbethoxyhydrazine in 55 ml n. pentylalcohol is warmed up to 140° C and kept at this temperature for 4 hours. After cooling the solution is extracted several times with water and then extracts collected together are extracted with ethyl ether. The aqueous phase is treated at room temperature with sodium bicarbonate until complete precipitation. The precipitate is collected, washed with water and dried under vacuum at room temperature on phosphorus pentaoxide to give with good yield 3-(2-carbethoxyhydrazino)-6-[N-(2-hydroxypropyl)ethylamino]-pyridazine melting at 160°–162° C.

Analysis:

Calculated for $C_{12}H_{21}N_5O_3$: C, 50.87; H, 7.47; N, 24.72. Found: C, 50.95; H, 7.57; N, 24.81.

What is claimed is:

1. 3-(2-Carbethoxyhydrazino)-6-[N-(2-hydroxypropyl)ethylamino]-pyridazine and its pharmaceutically acceptable salts.
2. Pharmaceutical composition comprising an antihypertensively effective amount of the compound according to claim 1 and an inert pharmaceutical carrier.

* * * * *

UNITED STATES PATENT AND TRADEMARK OFFICE
CERTIFICATE OF CORRECTION

PATENT NO. : 4,002,753
DATED : January 11, 1977
INVENTOR(S) : Carlo CARPI et al.

It is certified that error appears in the above-identified patent and that said Letters Patent are hereby corrected as shown below:

Under [75] Inventors:, change "S.Polo d'EnZa" to --S.Polo d'Enza--.

Column 3, line 31, change "cloroform" to --chloroform--;

Column 3, line 62, change "crstallized" to --crystallized--.

Column 4, line 61, change "oilis" to --oil is--.

*Signed and Sealed this*

Nineteenth Day of April 1977

[SEAL]

*Attest:*

RUTH C. MASON
*Attesting Officer*

C. MARSHALL DANN
*Commissioner of Patents and Trademarks*